United States Patent [19]

Näf

[11] 4,054,606

[45] Oct. 18, 1977

[54] PROCESS FOR THE PREPARATION OF KETONE DERIVATIVES

[75] Inventor: Ferdinand Näf, Geneva, Switzerland

[73] Assignee: Firmenich SA, Geneva, Switzerland

[21] Appl. No.: 580,525

[22] Filed: May 23, 1975

[30] Foreign Application Priority Data

May 31, 1974 Switzerland .................... 7476/74

[51] Int. Cl.$^2$ .................... C07C 45/00; C07C 45/15
[52] U.S. Cl. ............................ 260/586 C; 260/586 R; 260/617 A; 260/666 C
[58] Field of Search ................... 260/586 R, 586 C

[56] References Cited

U.S. PATENT DOCUMENTS

| 2,921,940 | 1/1960 | Ramsden ..................... 260/586 R |
| 3,876,706 | 4/1975 | Levanevsky et al. ........... 260/586 C |

*Primary Examiner*—Norman Morgenstern
*Attorney, Agent, or Firm*—Pennie & Edmonds

[57] ABSTRACT

Process for the preparation of α-substituted cyclic ketones which comprises reacting a magnesium enolate with an aldehyde. The products obtained in accordance with the process of the invention are useful intermediates for the preparation of perfume and flavor ingredients, as well as for the synthesis of certain carotenoids.

9 Claims, No Drawings

PROCESS FOR THE PREPARATION OF KETONE DERIVATIVES

BACKGROUND OF THE INVENTION

The addition of enolate anions to carbonyl functions constitutes one of the most important and widely used synthetic techniques in organic chemistry. In particular the aldol condensation, which namely consists in the addition of an enolate anion to a carbonyl group of a ketone or an aldehyde followed by a protonation, is a well known reaction [see e.g.: H. O. House, Modern Synthetic Reactions, 2nd Edition, W. A. Benjamin Inc. (1972), p. 629 and following]. This aldol condensation is usually effected in the presence of a basic or an acidic catalyst and, starting from a ketone or an aldehyde, yields as an intermediate reactive species, an enolate and an enol, respectively.

The reaction is characterized by a series of complex equilibria which, depending upon the nature of the reactants and of the catalysts chosen, often lead to the formation of complex reaction mixtures. In most instances, aldol condensation is in fact accompanied by concomitant dehydrations, retrograde reactions (or retroaldolisations), and polymerisations, and consequently its industrial application suffers from serious drawbacks. In order to obviate to these disadvantages, several specific methods have been developed in the past; however, so far, none of them could be satisfactorily applied to the reaction occurring between 3,3-dimethyl-cyclohexanone and an aldehyde of formula $$R-CHO \qquad (I)$$

wherein R represents a saturated, mono- or poly-unsaturated, linear or branced, substituted or unsubstituted univalent hydrocarbon or oxygen-substituted hydrocarbon radical.

The invention involves a novel process for producing substituted cyclic ketones, and it is therefore not important insofar as the process is concerned what "R" is, so long as the "R" constituent or group does not contain functional groups which will interfere with or prevent the reaction and that the CHO moiety remains functional. To date the applicant is unaware of any "R" constituent or group which cannot be used in the disclosed process.

Due to the interest presented by α-substituted cyclic ketone derivatives as intermediates for the preparation of certain perfume and flavour ingredients, as well as for the synthesis of certain carotenoids or related derivatives such as vitamin A or ionones, it is of primary importance to dispose of a synthetic procedure leading to a regioselective substitution in position α of an unsymmetrical ketone.

THE INVENTION

We have now discovered that such a regioselective substitution could easily be effected by the reaction between an enolate of formula

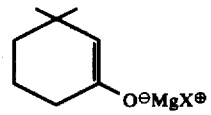

(II)

wherein X represents a halogen, e.g. bromine, chlorine or iodine, and an aldehyde of formula (I).

Consequently, it is an object of the present invention to provide a process for the preparation of an α-substituted cyclic ketone of formula

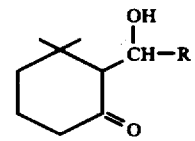

(III)

(wherein R is defined as indicated for formula (I)), which process comprises treating an enolate of formula (II) with an aldehyde of formula (I).

PREFERRED EMBODIMENTS OF THE INVENTION

According to a preferred embodiment of the invention, the reaction between the said enolate and aldehyde (II) can be carried out at a temperature of from about −15° to about 0° C. Although in most instances, temperatures situated in a slightly higher or lower range than the above given limits can be employed satisfactorily without any great noticeable difference in the product yields obtained, we have observed that, by operating within the temperature limits indicated, the formation of by-products was greatly suppressed and the final separation of the desired ketones made easy.

The said reaction can be performed in an inert organic solvent, preferably apolar or weakly polar. Suitable organic solvents include an ether, such as diethyl-ether, di-n-propyl-ether, diisopropyl ether, methyl-n-butyl-ether, ethyl-n-butyl-ether, or tetrahydrofuran, or any mixture comprising at least two of the aforementioned solvents. For practical and economical reasons, diethyl-ether is preferred. The enolates of formula (II) can be synthesized according to the usual synthetic techniques by treating 3-methyl-cyclohex-2-enone with a methyl-magnesium halide, preferably in the presence of a copper halide. A specific embodiment of the said method is better illustrated in one of the following examples.

Among the variety of ketone derivatives which can be synthesized by the process of the present invention, the following ones are of particular interest:

3,3-dimethyl-2-[1-hydroxy-ethyl]-cyclohexanone,
3,3-dimethyl-2-[1-hydroxy-but-2-en-1-yl]-cyclohexanone,
3,3-dimethyl-2-[1-hydroxy-3,7-dimethyl-octa-2,6-dien-1-yl]-cyclohexanone, and the compounds of formula

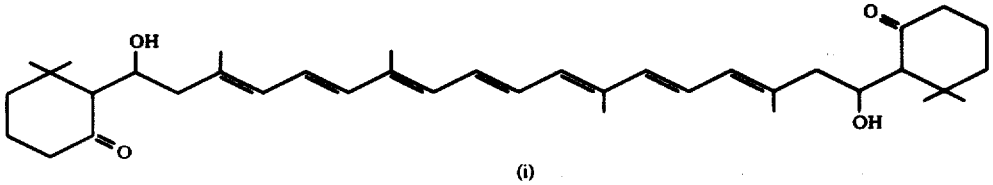

(i)

and of the formula

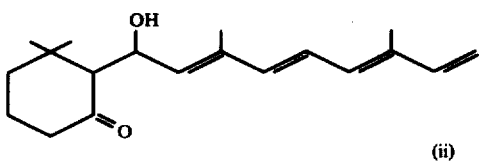

(ii)

these latter two compounds being useful intermediates for the preparation of β-carotene and vitamin A, respectively. Their utilization to this effect is illustrated by the following reaction scheme:

with 8.52 g (60mM) of methyl iodide in 40 ml of ether, 200 mg of copper$^I$-iodide were added at −5°. The reaction mixture was kept under stirring at this temperature during 5 min, whereupon 5.5 g (50 mM) of 3-meth-

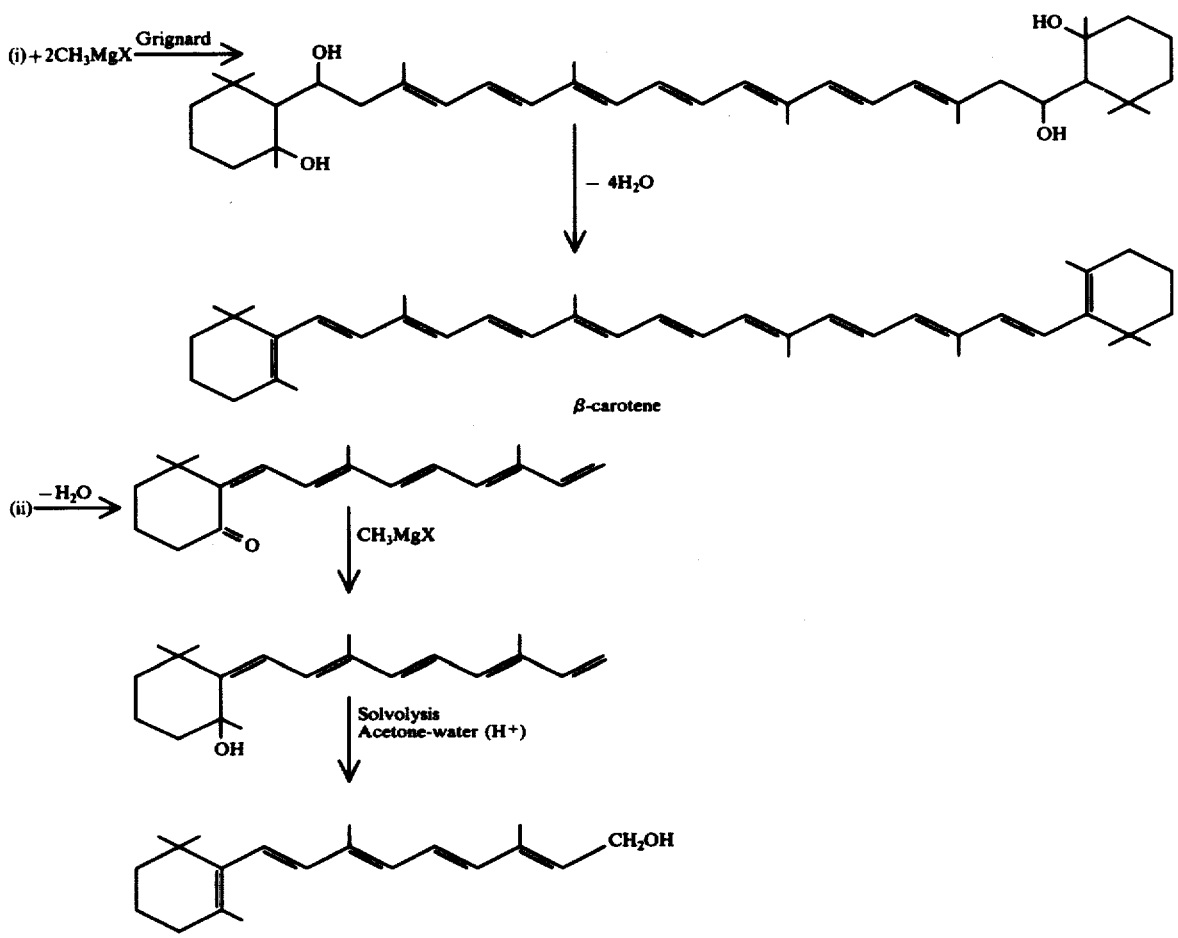

The invention is illustrated in a more detailed manner by, but not limited to the following examples wherein the temperatures are indicated in degrees centigrade and the abbreviations have the common meaning.

EXAMPLE 1

3,3-Dimethyl-2-[1-hydroxy-ethyl]-cyclohexanone

To a solution of methyl-magnesium iodide, prepared by reacting 1.44 g (60 matg) of magnesium turnings yl-cyclohex-2-en-1-one in 20 ml ether were added thereto while stirring for 30 more minutes. The temperature was then decreased to −15°/−10° and a solution of 2.2 g (50mM) of acetaldehyde in 10 ml of ether was added to the reaction mixture.

This latter was stirred for 30 min at 0°, then for 30 min more at 25° whereupon it was poured into a mixture of 2.5 ml of 2N hydrochloric acid and crushed ice. After extraction with ether, separation of the organic phase, followed by washing with a NaCl solution, drying over magnesium sulphate and evaporation, a residue was obtained, which by fractional distillation yielded 6.34 g (75 %) of 3,3-dimethyl-2-[1-hydroxy-ethyl]-cyclohexanone having a b.p. of 69°-73°/0.01 Torr.

NMR(90MHz): 1.05 (3H, s); 1.12 (3H, s); 1.3 (3H, d, J = 7Hz); 2.00-2.5 (2H, and 1H); 3.5 (1H, s); 4.10 (1H, d of q, J' = 6Hz, J" = 7 Hz) δ ppm.

MS : M+ = 170 (3); m/e: 152 (9), 126 (23), 111 (100), 95 (7), 83 (95), 69 (32), 55 (62), 43 (36), 41 (42), 39 (20), 29 (32).

The utility of the obtained compound as intermediate in the preparation of certain end products useful for the perfume industry, is illustrated by the following reaction scheme:

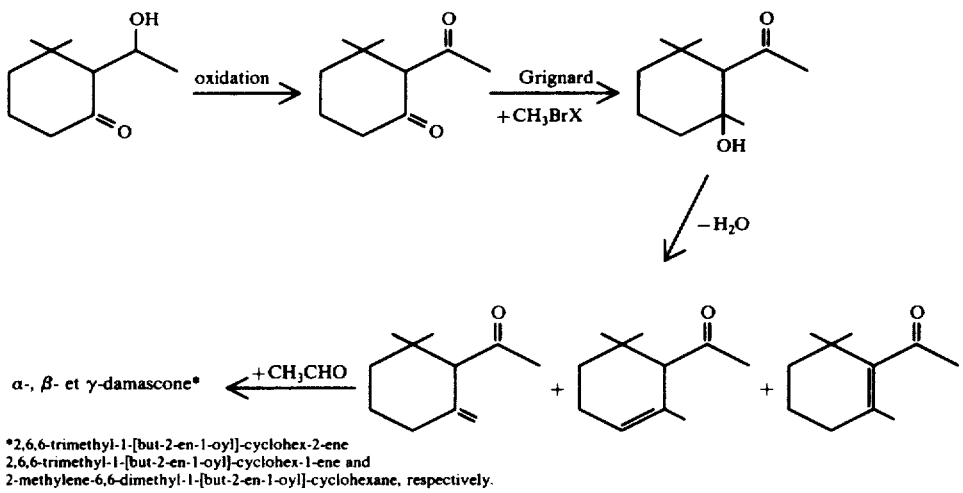

*2,6,6-trimethyl-1-[but-2-en-1-oyl]-cyclohex-2-ene
2,6,6-trimethyl-1-[but-2-en-1-oyl]-cyclohex-1-ene and
2-methylene-6,6-dimethyl-1-[but-2-en-1-oyl]-cyclohexane, respectively.

EXAMPLE 2

3,3-Dimethyl-2-[1-hydroxy-but-2-en-1-yl]-cyclohexanone

A solution of methyl-magnesium iodide was prepared from 1.44 g of magnesium turnings according to the procedure described in Example 1. 5.5g (50mM) of 3-methyl-cyclohex-2-en-1-one in 20 ml of ether were then slowly added under stirring at −5° to the reaction mixture, whereupon the temperature was decreased to −15°/−10° and a solution of 3.5 g (50 mM) of crotonaldehyde in 10 ml ether was added thereto.

The obtained reaction mixture was kept under stirring at 20° for 1h, then 25 ml of a 2N HCl solution were added thereto at 0°. After the usual treatments of extraction with ether, separation of the organic phase followed by washing, drying over MgSO₄ and evaporation, 10 g of the desired raw ketone were obtained.

A purification by fractional distillation yielded 5.54 g (57 %) of 3,3-dimethyl-2-[1-hydroxy-but-2-en-1-yl]cyclohexanone having a b.p. of 93°-6°/0.01 Torr. During this distillation a retroaldolisation was observed, which had as a consequence a lowering of the yield of the desired end product.

The title compound had the following analytical character:

NMR(60MHz): 0.98 (3H, s); 1.03 (3H, s); 2.5 (1H, d, J = 6 Hz); 2.93 (1H, s); 4.32 (1H, d de d, J' = 6Hz, J" = 7 Hz); 5.5-5.8 (2H, m) δ ppm;

IR (liq.) : 3450, 1690 cm⁻¹.

EXAMPLE 3

3,3-Dimethyl-2-[1-hydroxy-3,7-dimethyl-octa-2,6-dien-1-yl]-cyclohexanone

A solution of methyl-magnesium iodide was prepared as indicated in Example 1. 5.5 g (50 mM) of 3-methyl-cyclohex-2-en-1-one in 20 ml of ether were added under stirring at −5° to the reaction mixture. To this mixture, 7.6 g (50 mM) of citral in 10 ml of ether were added [the citral used consisted in a mixture containing 64 % of trans isomer and 36 % of cis isomer], whereupon the whole was kept under stirring 1 h at 20° and poured then into a mixture of 25 ml of a 2N solution of HCl and ice. The usual treatments (see Example 1) gave 13.4 g of 3,3-dimethyl-2-[1-hydroxy-3,7-dimethyl-octa-2,6-dien-1-yl]-cyclohexanone (96%), which analytical constants were as follows:

NMR(60MHz): 1.0 (3H, s); 1.1 (3H, s); 1.6 (3H, s); 1.65 (6H, s); 3.18 (1H, s); 4.6 (1H, m); 4.9-5.63 (1H and 1H, m); δ ppm IR (liq.) : 3460, 1695 cm⁻¹.

EXAMPLE 4

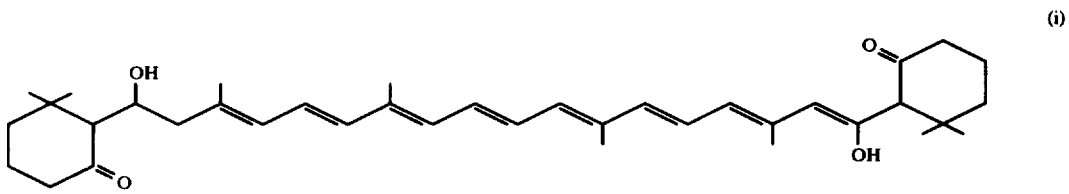

(i)

60 mM of magnesium enolate, prepared according to the method indicated in the hereinabove Examples starting from methyl magnesium iodide and 3-methyl-cyclohex-2-en-1-one, were treated with a solution of 8.1 g (25 mM) of 3,7,12,16-tetramethyl-octadeca-3,5,7,9,11,13,15-heptaen-1,18-dial in 20 ml of ether at −10°/−15°. The reaction mixture was kept under stirring at 20° during 1h, whereupon it was subjected to the usual treatments as described in the above Examples. 13 g (90 %) of the desired raw material were thus obtained.

The NMR spectrum of the obtained product was the following: NMR (60MHz): 1.05 (12 H, s); 1.7 (6H, s); 2.0 (6H, s); 4.1 (2H, d of t, J′ = 6 Hz, J″ = 7Hz); 5.8–6.85 (10H, m) δ ppm.

EXAMPLE 5

3,3-Dimethyl-2-[1-hydroxy-3,7-dimethyl-nona-2,4,6,8-tetraen-1-yl]-cyclohexanone 60 mM of magnesium enolate, prepared according to the method indicated in the hereinabove Examples starting from methyl magnesium iodide and 3-methyl-cyclohex-2-en-1-one, were treated with a solution of 8.1 g (50 mM) of 3,7-dimethyl-nona-2,4,6,8-tetraen-1-al in 10 ml of ether at about −10°.

The mixture was subjected to the same treatment as those described in the previous Example, in order to give 14 g (93 %) of the desired compoud. Its analytical data were the following:

NMR(60MHz): 0.95 (3H, s); 1.03 (3H, s); 2.5 (1H, d, J = 6.5 Hz); 4.3 (1H, d of d, J′ = 6Hz, J″ = 7Hz); 4.9–5.3 (2H); 6.1–6.8 (5H, m) δ ppm.

3,7-Dimethyl-nona-2,4,6,8-tetraen-1-al, used as starting material for the above preparation, could be synthesized from 6-methyl-2-oxo-octa-3,5,7-triene according to the method described by Wittig and Frommeld, Chem. Ber., 97, 3548 (1964).

6-Methyl-2-oxo-octa-3,5,7-triene was prepared according to J. Chem. Soc., (1949) 2031 and J. Chem. Soc., (1952), 1094.

What we claim is:

1. A process for the preparation of α-substituted cyclic ketone compounds, of the formula

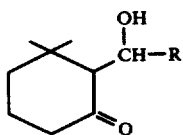

(III)

wherein R represents a saturated, a mono- or polyunsaturated, linear or branched, substituted or unsubstituted univalent hydrocarbon radical; which comprises reacting an enolate of formula

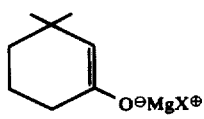

(II)

wherein X represents a halogen, with an aldehyde of the formula

R—CHO  (I)

wherein R is as defined above;
wherein the reaction is effected at a temperature of from about −15° to about 0° C, is carried out in an inert apolar or weakly polar organic solvent, and wherein the condensation products are subject to acidification.

2. A process according to claim 1 wherein an enolate of formula II is reacted with an aldehyde selected from the group consisting essentially of acetaldehyde, crotonaldehyde, citral, 3,7,12,16-tetra-methyl-octadeca-3,5,7,9,11,13,-15-heptaen-1,18-dial and 3,7-dimethyl-nona-2,4,6,8-tetraen-1-al.

3. A process according to claim 1, wherein the organic solvent is a dialkyl-ether.

4. A process according to claim 3, wherein the dialkyl-ether is diethyl ether.

5. A process according to any of claim 1, wherein the aldehyde of formula (I) is acetaldehyde and the obtained cyclic ketone of formula (III) is 3,3-dimethyl-2-[1-hydroxy-ethyl]-cyclohexanone.

6. A process according to any of claims 1, wherein the aldehyde of formula (I) is crotonaldehyde and the obtained cyclic ketone of formula (III) is 3,3-dimethyl-2-[1-hydroxy-but-2-en-1-yl]-cyclohexanone.

7. A process according to any of claim 1, wherein the aldehyde of formula (I) is citral and the obtained cyclic ketone is 3,3-dimethyl-2-[1-hydroxy-3,7-dimethyl-octa-2,6-dien-1-yl]-cyclohexanone.

8. A process according to any of claim 1, wherein the aldehyde of formula (I) is 3,7,12,16-tetramethyloctadeca-3,5,7,9,11,13,15-heptaen-1,18-dial and the obtained cyclic ketone is the compound of formula

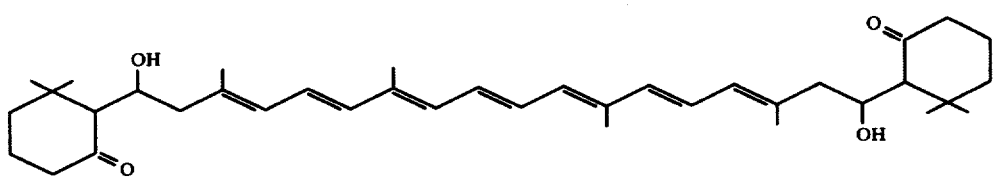

(i)

9. A process according to any of claim 1, wherein the aldehyde of formula (I) is 3,7-dimethyl-nona-2,4,6,8-tetraen-1-al and the obtained cyclic ketone is 3,3-dimethyl-2-[1-hydroxy-3,7-dimethyl-nona-2,4,6,8-tetraen-1-yl]-cyclohexanone.

* * * * *